(12) United States Patent
Bowyer et al.

(10) Patent No.: US 10,231,928 B2
(45) Date of Patent: Mar. 19, 2019

(54) DISC BRAKE ARRANGEMENT

(71) Applicant: SAF-HOLLAND, Inc., Holland, MI (US)

(72) Inventors: John Bowyer, Whitehall, MI (US); Edward Hammer, Muskegon, MI (US); Sean O'Brien, Grand Haven, MI (US)

(73) Assignee: SAF-HOLLAND, Inc., Holland, MI (US)

( * ) Notice: Subject to any disclaimer, the term of this patent is extended or adjusted under 35 U.S.C. 154(b) by 73 days.

(21) Appl. No.: 15/250,298

(22) Filed: Aug. 29, 2016

(65) Prior Publication Data

US 2017/0066426 A1 Mar. 9, 2017

Related U.S. Application Data

(60) Provisional application No. 62/215,425, filed on Sep. 8, 2015.

(51) Int. Cl.
*A61K 9/10* (2006.01)
*A61K 9/14* (2006.01)
*A61K 38/14* (2006.01)

(52) U.S. Cl.
CPC ............ *A61K 9/10* (2013.01); *A61K 9/14* (2013.01); *A61K 38/14* (2013.01)

(58) Field of Classification Search
CPC .... F16D 65/0056; F16D 65/008; F16D 65/00; F16D 65/005; F16D 55/225
USPC .......................................... 188/71.1
See application file for complete search history.

(56) References Cited

U.S. PATENT DOCUMENTS

| 2005/0023088 A1* | 2/2005 | Gripemark | F16D 55/24 188/73.31 |
| 2012/0247885 A1* | 10/2012 | Lantz | F16D 65/00 188/205 R |
| 2016/0076610 A1* | 3/2016 | White | F16D 65/00 188/73.39 |
| 2016/0356329 A1* | 12/2016 | Corcoran | F16D 65/0056 |

* cited by examiner

*Primary Examiner* — Melanie Torres Williams
(74) *Attorney, Agent, or Firm* — Price Heneveld LLP

(57) ABSTRACT

A vehicle braking arrangement includes an axle member, a brake torque plate having a first portion fixedly coupled to the axle member, and a second portion laterally offset from the first portion, and a brake caliper member coupled to the second portion of the brake torque plate such that the first portion of the brake torque plate is spaced from the brake caliper.

18 Claims, 8 Drawing Sheets

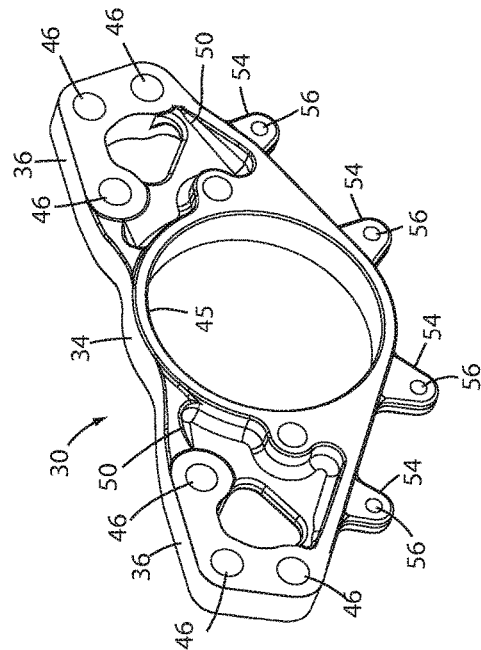
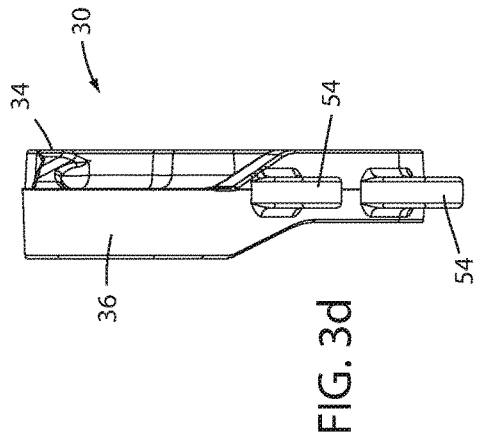
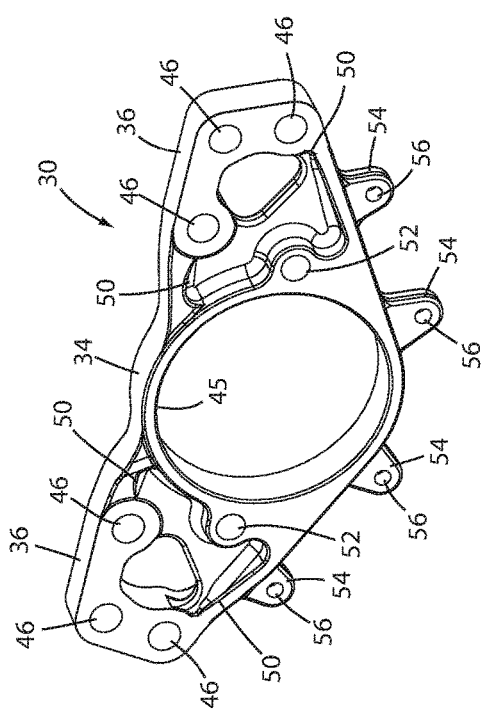
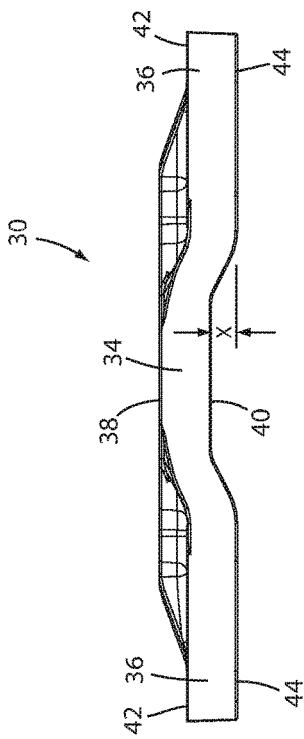
FIG. 3b
FIG. 3d
FIG. 3a
FIG. 3c

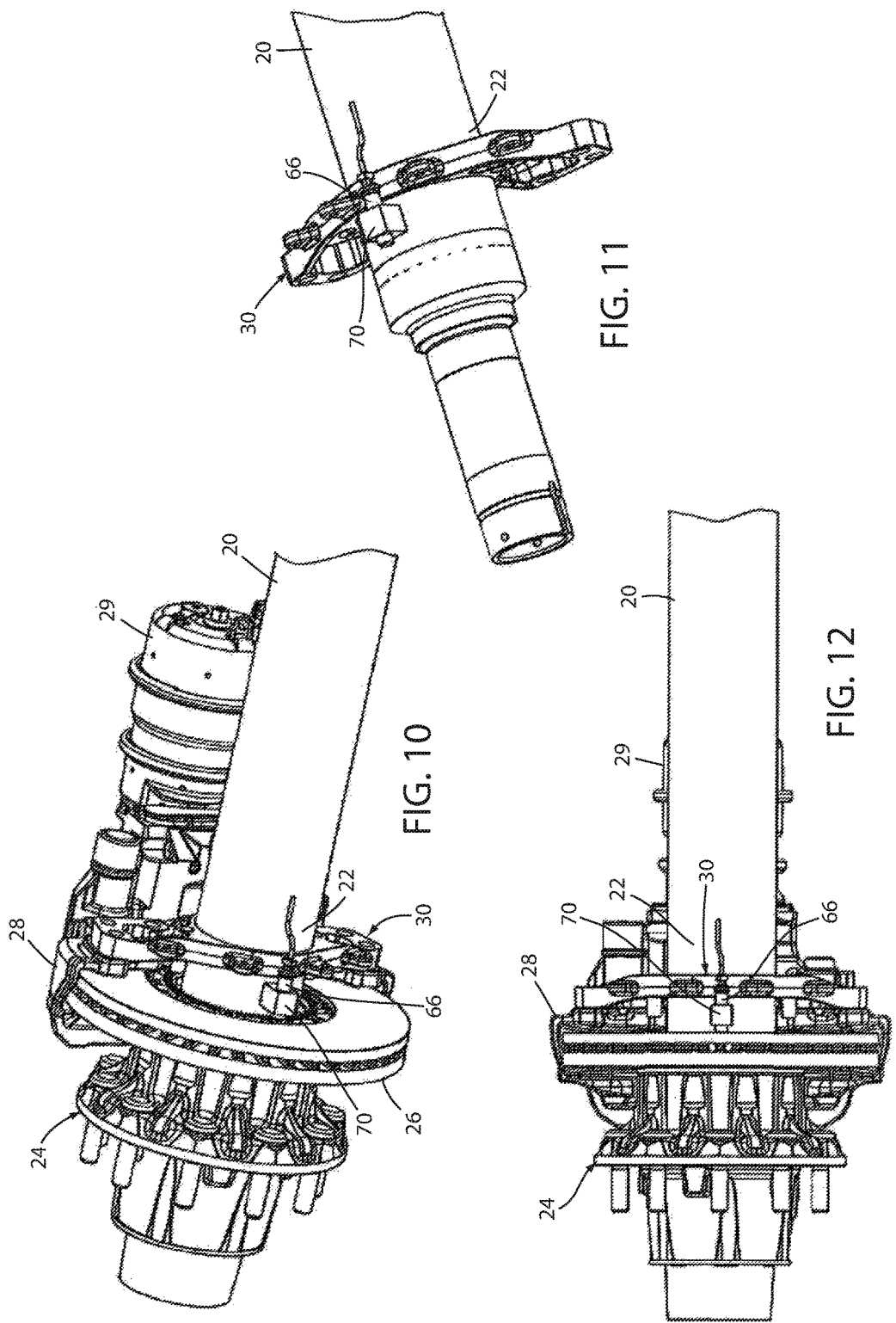

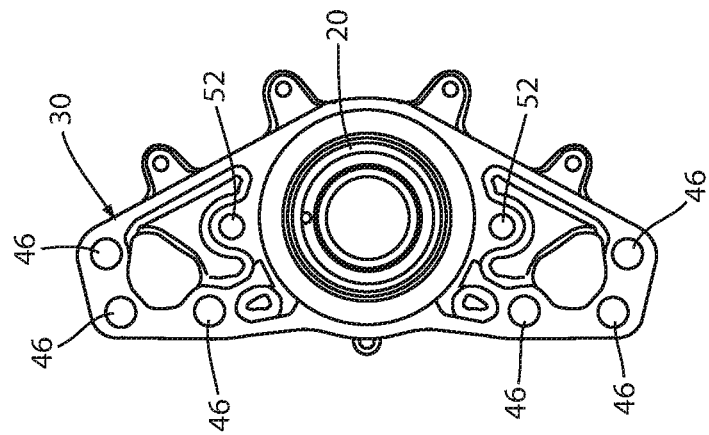
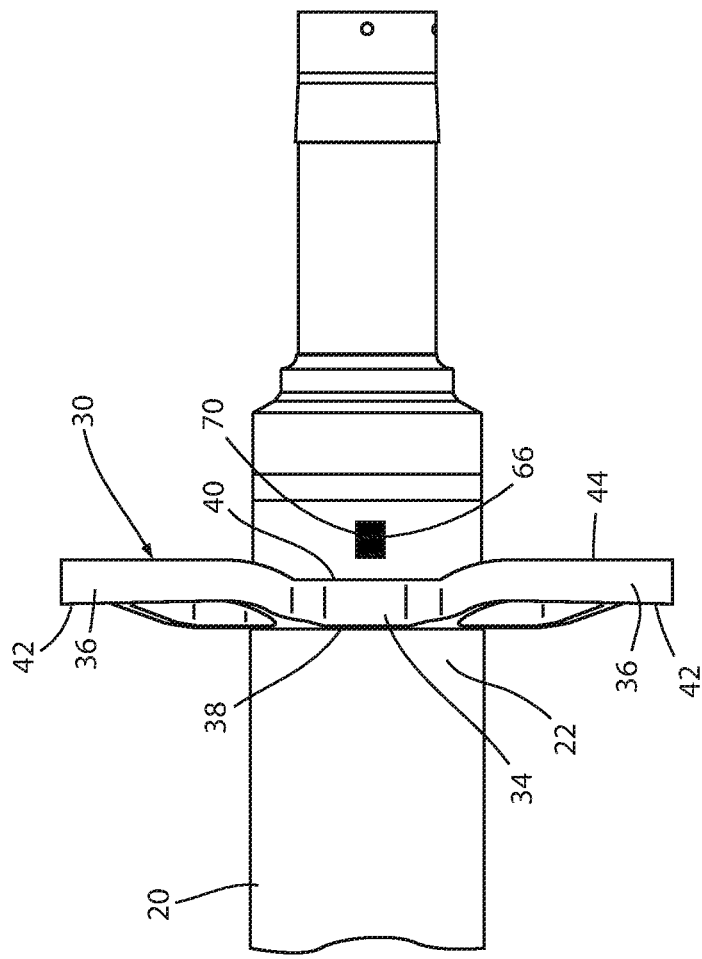

DISC BRAKE ARRANGEMENT

BACKGROUND OF THE INVENTION

The present invention relates to a disc brake arrangement, and in particular to a disc brake arrangement that includes an anti-lock braking system and a brake torque plate for mounting components of the anti-lock braking system to the associated suspension system.

BRIEF SUMMARY OF THE INVENTION

One embodiment comprises a vehicle braking arrangement that includes an axle member, a brake torque plate having a first portion fixedly coupled to the axle member, and second portion laterally offset from the first portion, and a brake caliper member coupled to the second portion of the brake torque plate such that the first portion of the brake torque plate is spaced from the brake caliper.

The present inventive vehicle braking system includes a mounting arrangement that is adapted for the proximate location of anti-lock braking sensors near an associated anti-lock braking system exciter ring and eliminates the necessity for alternative mounting arrangements that are relatively more complex and more expensive.

These and other features, advantages, and objects of the present invention will be further understood and appreciated by those skilled in the art by reference to the following specification, claims, and appended drawings.

BRIEF DESCRIPTION OF THE DRAWINGS

FIG. 3a is a first perspective view of the brake torque plate;

FIG. 3b is a second perspective view of the brake torque plate;

FIG. 3c is a top view of the brake torque plate;

FIG. 3d is an end view of the brake torque plate;

FIG. 10 is a perspective view of a brake disc arrangement with a second embodiment of the brake torque plate;

FIG. 11 is a perspective view of the second embodiment of the brake torque plate attached to an axle member;

FIG. 12 is a front elevational view of the second embodiment of the brake torque plate attached to an axle member;

FIG. 13 is a top plan view of the second embodiment of the brake torque plate attached to an axle member; and FIG. 14 is an end elevational view of the second embodiment of the brake torque plate attached to an axle member.

DETAILED DESCRIPTION OF THE PREFERRED EMBODIMENTS

Figure 1:
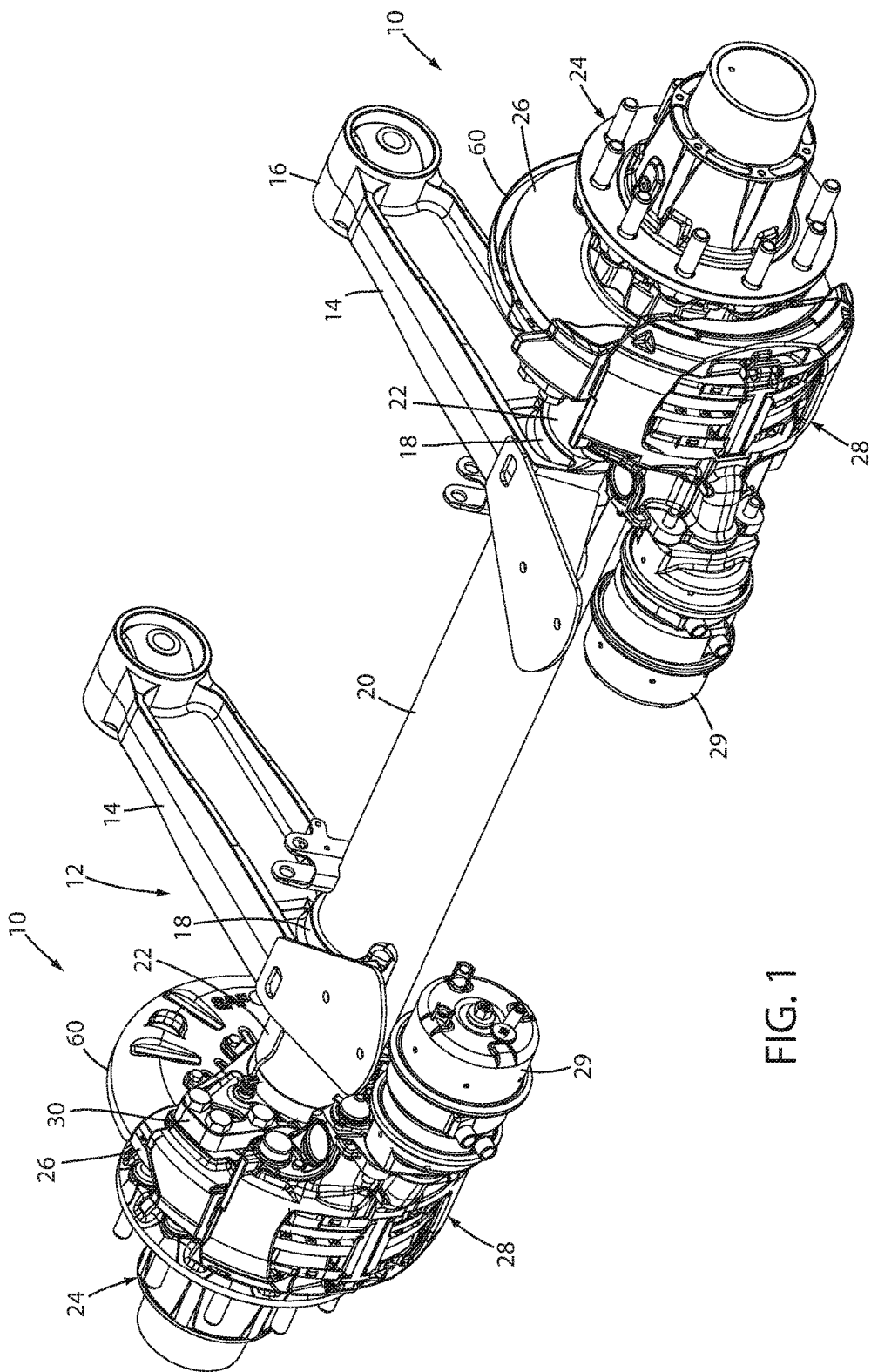
FIG. 1 is a perspective view of a disc brake arrangement and a trailing arm suspension arrangement.

For purposes of description herein, the terms "upper," "lower," "right," "left," "rear," "front," "vertical," "horizontal," and derivatives thereof shall relate to the invention as oriented in FIG. 1. However, it is to be understood that the invention may assume various alternative orientations and step sequences, except where expressly specified to the contrary. It is also to be understood that the specific devices and processes illustrated in the attached drawings, and described in the following specification are exemplary embodiments of the inventive concepts defined in the appended claims. Hence, specific dimensions and other physical characteristics relating to the embodiments disclosed herein are not to be considered as limiting, unless the claims expressly state otherwise.

Figure 2:
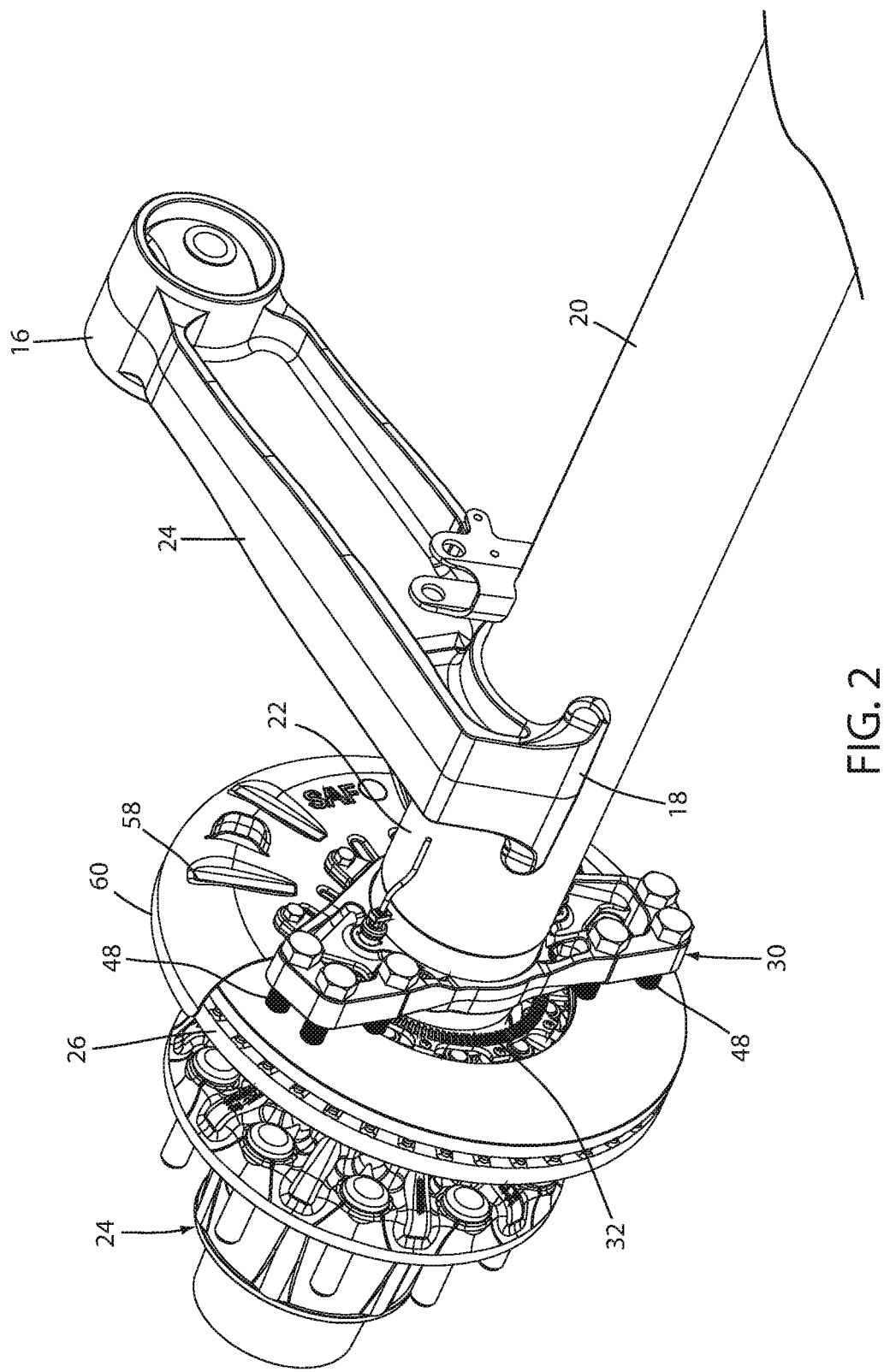
FIG. 2 is an enlarged perspective view of the disc brake arrangement and the trailing arm suspension arrangement with component removed to show a brake torque plate.
Figure 4:
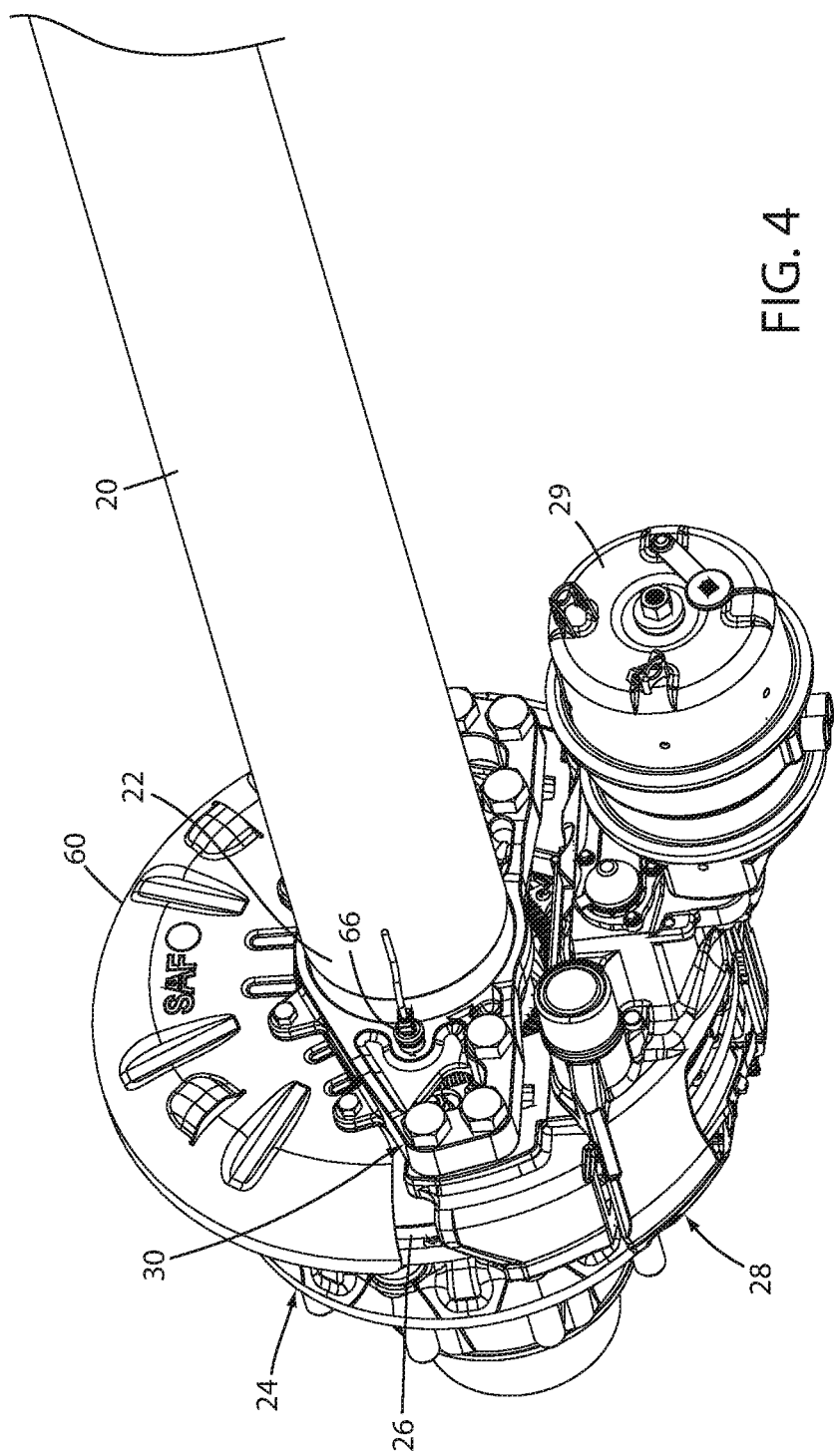
FIG. 4 is a perspective view of a brake disc arrangement with a first embodiment of the brake torque plate.
Figure 6:
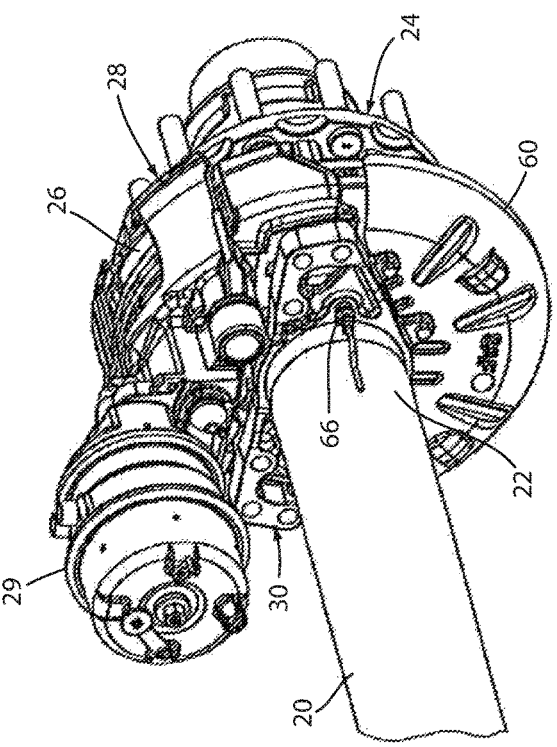
FIG. 6 is a perspective view of the brake disc arrangement with the first embodiment of the brake torque plate.
Figure 5:
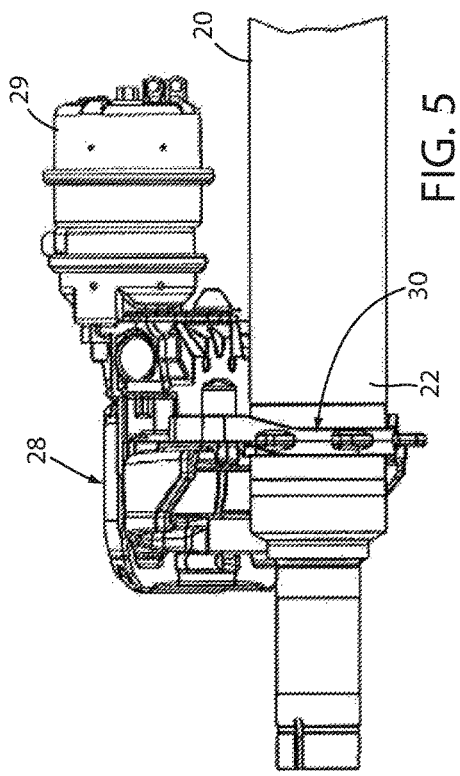
FIG. 5 is a top plan view of the brake disc arrangement and the first embodiment of the brake torque plate.
Figure 7:
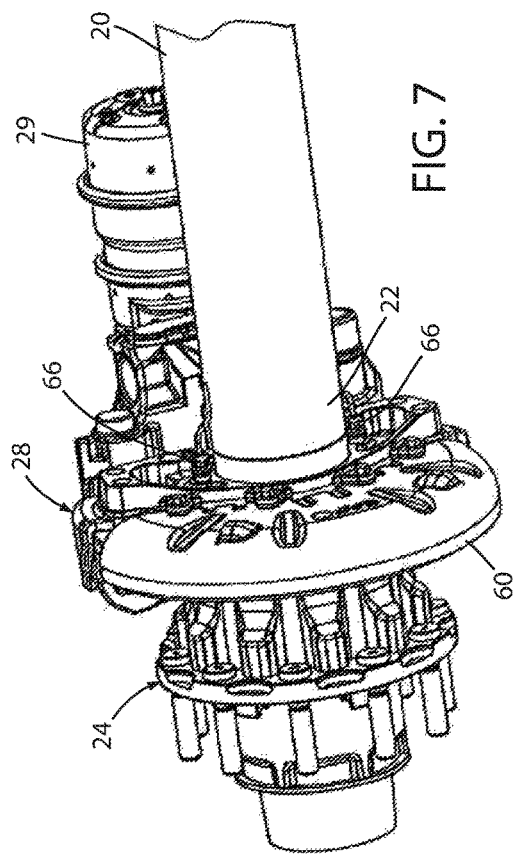
FIG. 7 is a perspective view of the brake disc arrangement with the first embodiment of the brake torque plate.
Figure 9:
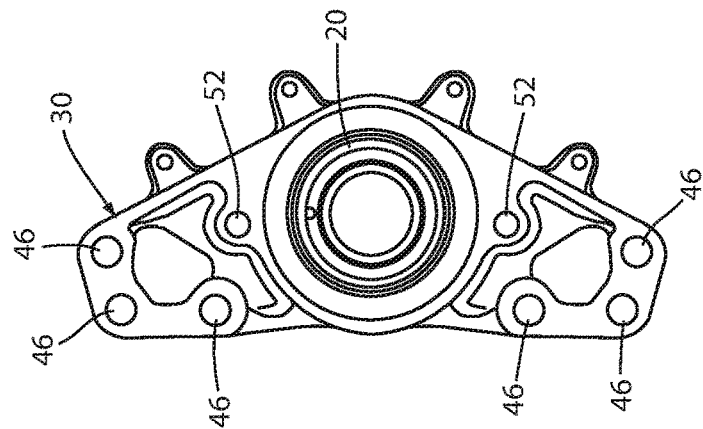
FIG. 9 is an end elevational view of the first embodiment of the brake torque plate attached to an axle member.
Figure 8:
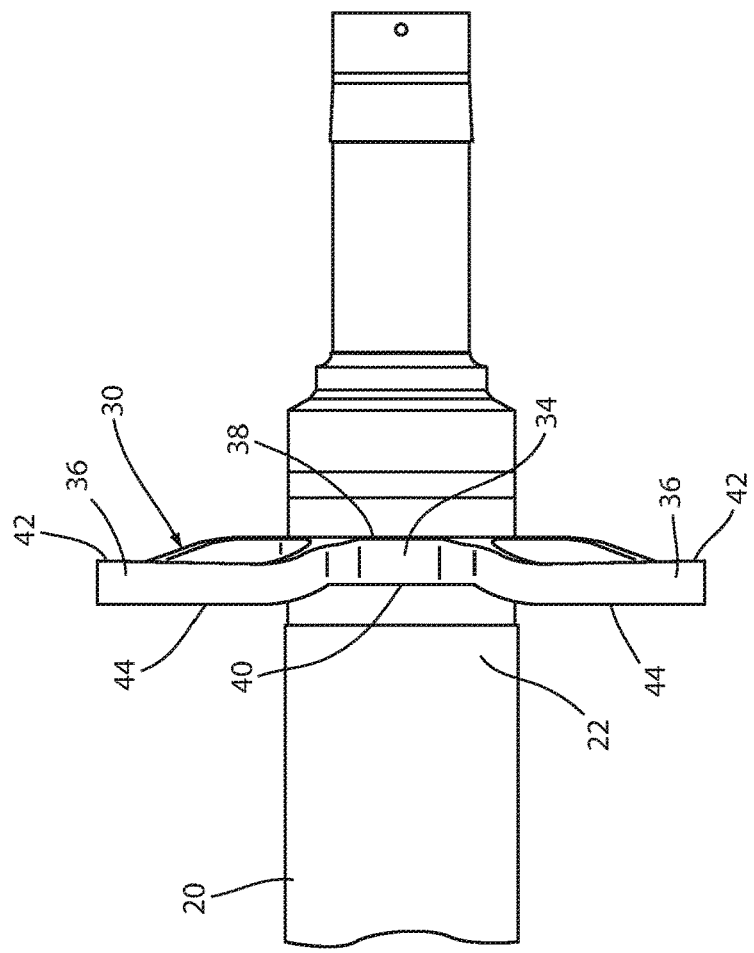
FIG. 8 is a top plan view of the first embodiment of the brake torque plate attached to an axle member.

A pair of disc brake arrangements 10 (FIG. 1) illustrating an embodiment of the present invention are shown in conjunction with a trailing arm suspension arrangement 12. The trailing arm suspension arrangement 12 includes a pair of trailing arm members 14 each having a first end 16 configured to pivotably couple with a mounting bracket (not shown) which is in turn configured to couple to a vehicle frame member (not shown). Each trailing arm member 14 further includes a second end 18 fixedly coupled to an axle member 20. The axle member 20 includes opposite ends 22 to which the disc brake arrangements 10 are coupled. A hub assembly 24 and a brake disc 26 are pivotably coupled to each of the opposite ends 22 of the axle member 20 via a spindle assembly (not shown). The disc brake arrangement 10 includes a brake disc or rotor 26, and a brake caliper 28 mounted to the axle member 20 by a brake spider or brake torque plate 30. The brake torque plate 30 (FIG. 2) is located near an anti-lock braking system (ABS) exciter ring 32. A pneumatic brake actuator 29 is provided to actuate the disc brake arrangement 10 in a conventional manner.

As best illustrated in FIGS. 3a-3d, the brake torque plate 30 includes a central or first portion 34 and a pair of second or end portions 36 juxtaposed from one another across the first portion 34 and extending outwardly therefrom. In the illustrated example, the first portion 34 includes a first surface 38 and a second surface 40 that cooperate to define the thickness of the first portion 34 therebetween, while each of the second portions 36 includes a first surface 42 and a second surface 44 that cooperate to define a thickness of the second portions 36 therebetween. It is noted that the first surface 38 of the first portion 34 is laterally offset from the first surface 42 of the second portion 36 by a distance X. The first portion 34 of the brake torque plate 30 includes a centrally disposed aperture 45 that receives an end 22 of the axle member 20 therein. The torque plate 30 is weldably secured to the axle member 20. The torque plate 30 further includes a plurality of apertures 46 positioned to receive mounting hardware such as bolts 48 (FIG. 2) therein to mount the caliper 28 to the brake torque plate 30. The brake torque plate 30 further includes a plurality of reliefs or apertures 50 provided to reduce the overall weight of the brake torque plate 30. The brake torque plate 30 further includes a pair of sensor receiving apertures 52 configured to receive ABS sensors, as described further below. The brake torque plate 30 still further includes a plurality of tabs 54 spaced about an outer periphery thereof and each including an aperture 56 that receives a corresponding mechanical fastener such as a bolt 58 (FIG. 2) that secures a rotor shroud 60 to brake torque plate 30.

As best illustrated in FIGS. 4-9, a first embodiment of the brake torque plate 30 is configured with the axle member 20 such that the first surface 38 of the first portion 34 is positioned laterally outboard of the first surface 42 of the second portion 36, thereby allowing for proper placement and spacing of the ABS sensor 66 from the associated ABS exciter ring 32. In the illustrated example, the ABS sensors 66 are mounted within the apertures 52 of the brake torque plate 30.

In an alternative embodiment, the brake torque plate 30 (FIGS. 10-14) is attached to the end 22 of the axle member 20 such that the first surface 38 of the first portion 34 is located inboard of the first surface 42 of the second portion 36, thereby allowing for a sensor mounting block 70 to be positioned between the brake torque plate 30 and the ABS exciter ring 32.

In the foregoing description, it will be readily appreciated by those skilled in the art that modifications may be made to the invention without departing from the concepts disclosed herein. Such modifications are to be considered as included in the following claims, unless these claims by their language expressly state otherwise.

The invention claimed is:

1. A vehicle braking arrangement, comprising:
   an axle member;
   a brake torque plate having a first portion fixedly coupled to the axle member and including a first outer surface and a first inner surface, and second portion laterally offset from the first portion and including a second outer surface and a second inner surface, wherein the first outer surface defines an outermost surface of the brake torque plate; and
   a brake caliper member coupled to the second portion of the brake torque plate such that the first portion of the brake torque plate is at least partially axially aligned with and spaced from the brake caliper.

2. The vehicle braking arrangement of claim 1, wherein at least a portion of the first portion is positioned laterally outboard of the second portion.

3. The vehicle braking arrangement of claim 2, wherein a majority of the first portion is positioned laterally outboard of the second portion.

4. The vehicle braking arrangement of claim 2, further comprising:
   an ABS brake sensor coupled to the first portion of the brake torque plate.

5. The vehicle braking arrangement of claim 1, further comprising:
   an ABS brake sensor coupled to the first portion of the brake torque plate.

6. The vehicle braking arrangement of claim 1, wherein at least a portion of the first portion is positioned laterally inboard of the second portion.

7. The vehicle braking arrangement of claim 6, wherein a majority of the first portion is positioned laterally inboard of the second portion.

8. The vehicle braking arrangement of claim 1, further comprising:
   a mounting bracket attached to the brake torque plate or directly to the axle positioned laterally outboard of the brake torque plate; and
   an ABS brake sensor coupled to the mounting bracket.

9. A brake torque plate, comprising:
   a first portion having a first inner surface and a first outer surface, the first portion configured to couple to an axle member; and
   a second portion having a second inner surface and a second outer surface configured to couple to a brake caliper, wherein at least one of the first inner surface is laterally inset from the second inner surface and the first outer surface is laterally outset from the second outer surface, and wherein the first outer surface defines an outermost surface of the brake torque plate.

10. The brake torque plate of claim 9, wherein the first inner surface is laterally inset from the second inner surface, and wherein the first outer surface is laterally inset from the second outer surface.

11. The brake torque plate of claim 10, wherein the first portion includes an aperture configured to receive an axle member.

12. The brake torque plate of claim 11, wherein the first portion is configured to couple to an ABS brake sensor.

13. The brake torque plate of claim 9, wherein the first portion includes at least one aperture configured to couple to an ABS brake sensor.

14. The brake torque plate of claim 9, wherein the first portion includes an aperture configured to receive an axle member.

15. The brake torque plate of claim 9, wherein the first portion is configured to couple to an ABS brake sensor.

16. The brake torque plate of claim 15, wherein the first portion includes at least one aperture configured to couple to an ABS brake sensor.

17. The brake torque plate of claim 9, wherein the first inner surface is laterally outset from the second inner surface, and wherein the first outer surface is laterally outset from the second outer surface.

18. A vehicle braking arrangement, comprising:
   an axle member;
   a brake torque plate having a first portion fixedly coupled to the axle member and including a first outer surface and a first inner surface, and second portion laterally offset from the first portion and including a second outer surface and a second inner surface, wherein the first outer surface is positioned more laterally outward than a remainder of the brake torque plate; and
   a brake caliper member coupled to the second portion of the brake torque plate such that the first portion of the brake torque plate is at least partially axially aligned with and spaced from the brake caliper.

* * * * *